US00PP33209P2

(12) United States Plant Patent
Hochberg

(10) Patent No.: US PP33,209 P2
(45) Date of Patent: Jun. 29, 2021

(54) ***LAGERSTROEMIA* PLANT NAMED 'HOCH873'**

(50) Latin Name: *Lagerstroemia indica*
Varietal Denomination: HOCH873

(71) Applicant: Hochberg Ornamental Export Plants Ltd, Moshav Bitzaron (IL)

(72) Inventor: Omer Hochberg, Moshav Bitzaron (IL)

(73) Assignee: Hochberg Ornamental Export Plants Ltd

( * ) Notice: Subject to any disclaimer, the term of this patent is extended or adjusted under 35 U.S.C. 154(b) by 0 days.

(21) Appl. No.: 17/094,142

(22) Filed: Nov. 10, 2020

(51) Int. Cl.
*A01H 5/02* (2018.01)
*A01H 6/00* (2018.01)

(52) U.S. Cl.
USPC ..... Plt./252
CPC ..... *A01H 6/00* (2018.05)

(58) Field of Classification Search
USPC ..... Plt./252
CPC ..... A01H 6/00
See application file for complete search history.

*Primary Examiner* — Anne Marie Grunberg
(74) *Attorney, Agent, or Firm* — Cassandra Bright

(57) ABSTRACT

A new and distinct cultivar of *Lagerstroemia* plant named 'HOCH873' is disclosed, characterized by white flowers, and black foliage. Plants are upright in form and have been observed resistant to powdery mildew. The new variety is a *Lagerstroemia*, normally used for outdoor ornamental purposes.

1 Drawing Sheet

Latin name of the genus and species: *Lagerstroemia indica.*

Variety denomination: 'HOCH873'.

BACKGROUND OF THE INVENTION

The new *Lagerstroemia* cultivar is a product of a planned breeding program conducted by the inventor, in Moshav Bitzaron, Israel. The objective of the breeding program was to develop new Crepe Myrtle plants for ornamental purposes. The cross resulting in this new variety was made during July of 2015.

The seed parent is the unpatented proprietary variety referred to as *Lagerstroemia* 'L92'. The pollen parent is the unpatented proprietary variety referred to as *Lagerstroemia* 'L88'. The new variety was selected in August of 2016 by the inventor in a group of seedlings resulting from the 2015 crossing, in a nursery in Moshav Bitzaron, Israel. Date of first sale was Jan. 1, 2020, occurring in Europe. This sale was made directly by the inventor or one who obtained the claimed invention directly or indirectly from the inventor. This sale and all public disclosures made between Jan. 1, 2020 and the filing of this application fall within the exception allowed under 102(b)(1).

Asexual reproduction of the new cultivar was performed by softwood cuttings. This was first performed at the same nursery in Moshav Bitzaron, Israel during June of 2017, and has shown that the unique features of this cultivar are stable and reproduced true to type in multiple successive generations.

SUMMARY OF THE INVENTION

The cultivar 'HOCH873' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'HOCH873' These characteristics in combination distinguish 'HOCH873' as a new and distinct *Lagerstroemia* cultivar:

1. White blooms.
2. Black foliage.
3. Continuous bud and flower formation throughout the Summer.
4. Upright plant habit, reaching 70 to 90 cm in the second year.

PARENT COMPARISON

Plants of the new cultivar 'HOCH873' are similar to plants of the seed parent in most horticultural characteristics; however, plants of the new cultivar 'HOCH873' differ in the following;

1. The new variety has white flowers, while the seed parent has light pink flowers.

Plants of the new cultivar 'HOCH873' are similar to plants of the pollen parent in most horticultural characteristics; however, plants of the new cultivar 'HOCH873' differ in the following;

1. The new variety has an upright plant form; the pollen parent is mounding.
2. Foliage of the new variety is black; foliage of the pollen parent is green.

COMMERCIAL COMPARISON

Plants of the new cultivar 'HOCH873' are comparable to the commercial variety *Lagerstroemia* 'Best Red', unpatented. The two *Lagerstroemia* varieties are similar in most horticultural characteristics; however, the new variety 'HOCH873' differs in the following;

1. The new variety has white blooms; this comparator has red blooms.
2. The new variety has resistance to powdery mildew.

Plants of the new cultivar 'HOCH873' are comparable to the commercial variety *Lagerstroemia* 'Rhapsody in Pink', U.S. Plant Pat. No. 16,616. The two *Lagerstroemia* varieties are similar in most horticultural characteristics; however, the new variety 'HOCH873' differs in the following;

1. The new variety has white blooms, while this comparator has pink blooms.
2. The new variety has black foliage; this comparator has green foliage.

BRIEF DESCRIPTION OF THE PHOTOGRAPH

The accompanying photograph illustrates multiple typical flowering plants of 'HOCH873' grown outdoors in Moshav Bitzaron, Israel. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'HOCH873' plants grown outdoors in Visalia, Calif. The growing temperature ranged from approximately 18° C. to 38° C. during the day and from approximately 5° C. to 10° C. during the night. General light conditions are normal sunlight and numerical values represent averages of typical plant types. Measurements were taken during June of 2020.

Botanical classification: *Lagerstroemia indica* 'HOCH873'.

PROPAGATION

Type of propagation typically used: Softwood cuttings.
Time to initiate roots: 21 days at 18-27° C.
Time to produce a rooted cutting: 1-2 months at 18-27° C.
Root description: Thin fibrous, dense, moderate branching. White in color, not accurately measured with R.H.S. Chart.

PLANT

Age of plant described: About 1.5 years old from a rooted cutting.
Container size: 3 gallon container.
Growth habit: Upright.
Plant spread: 35 cm.
Plant height: 70 to 90 cm.
Plant vigor: Good.
Length of primary lateral branches: Varies as the plant is often pruned. 20 to 40 cm on average.
Diameter of lateral branches: 4 to 7 mm.
Quantity of lateral branches: About 10 to 14.
Stem:
- *Color*.—New growth: Near RHS Greyed-Purple 183A. Old growth: Near RHS Red-Purple 187B, flushed 187A.
- *Shape*.—Round.
- *Strength*.—Good, flexible and strong.
- *Aspect angle*.—Upright.
- *Texture*.—Very slightly pubescent, then scaly with age.

Internode length: Average range 0.6 to 2.0 cm.
Bark peel: Base of the oldest wood develops a scaly, non-peeling bark colored near Brown N200B striped Greyed-Orange 177A.

FOLIAGE

Leaf:
- *Arrangement*.—Sub-opposite.
- *Average length*.—4.5 cm.
- *Average width*.—2.5 cm.
- *Shape of blade*.—Ovate.
- *Apex*.—Acute.
- *Base*.—Obtuse.
- *Margin*.—Entire to finely serrate.
- *Aspect*.—Undulate.
- *Texture of top surface*.—Smooth.
- *Texture of bottom surface*.—Smooth.
- *Color*.—Young foliage upper side: Near RHS Yellow-Green 147A flushed Greyed-Purple N186A. Young foliage under side: Near RHS Yellow-Green 147B flushed Greyed-Purple N186B. Mature foliage upper side: Near RHS Black 202A. Mature foliage under side: Near RHS Greyed-Purple N186A to Black 202A. Venation: Type: Pinnate. Venation color upper side: Near RHS Greyed-Purple N186C. Venation color under side: Near RHS Greyed-Purple 186C.
- *Petiole*.—Length: 1 mm. Diameter: 1 mm. Texture, upper side: Smooth. Texture, under side: Smooth. Color, upper side: Near RHS Greyed-Purple N186C. Color, under side: Near RHS Greyed-Purple N186C.

FLOWER

Natural flowering season: Summer through Fall. Begins flowering mid-June in California.
Inflorescence form: Panicles.
Flowers per inflorescence: About 70 to 120 flowers and buds.
Inflorescence size:
- *Width*.—9 cm.
- *Length*.—Average 12 cm.

Individual flowers:
- *Type*.—Rotate.
- *Shape*.—Obovate.
- *Habit*.—Whorled outward.
- *Diameter*.—4.8 cm.
- *Depth*.—2.5 cm.
- *Persistence*.—Self-cleaning.
- *Fragrance*.—Faint floral scent.

Petals:
- *Arrangement*.—Whorled.
- *Number*.—6.
- *Shape*.—Overall irregular orbicular.
- *Aspect*.—Deeply undulate.
- *Margin*.—Deeply ruffled, crenate.
- *Tip shape*.—Rounded.
- *Base shape*.—Rounded.
- *Length*.—1.5 cm, undulated, cannot unfold.
- *Width*.—1.5 cm, undulated, cannot unfold.
- *Texture*.—Upper: Glabrous. Lower: Glabrous.
- *Color*.—When opening: Upper surface: Near RHS White N155D. Under surface: Near RHS White N155D. Fully opened: Upper surface: Near RHS White 155D. Under surface: Near RHS White 155D.

Bud:

*Shape*.—Sphere.
*Length*.—7 mm.
*Diameter*.—7 mm.
*Color*.—Near RHS Greyed-Purple 187B, base Green 139C.

Calyx:

*Shape*.—Fused into a conical shape.
*Length*.—12 mm.
*Diameter*.—11 mm.

Sepals:

*Appearance*.—Matte.
*Arrangement*.—Rotate, fused.
*Shape*.—Narrowly triangular.
*Tip shape*.—Acute.
*Base shape*.—Obtuse.
*Margin*.—Entire.
*Quantity per flower*.—6.
*Length*.—12 mm.
*Width*.—5 mm.
*Margin*.—Entire.
*Texture*.—Inner: Smooth. Outer: Smooth, coriaceous.
*Color*.—Inner: Near RHS Yellow-Green 147C flushed Greyed-Purple 186C in center. Apex 147A. Lower: Lower 50% near Green 139B, upper 50% near Greyed-Purple N186D.

Peduncle:

*Length*.—Average range 1.5 to 3.0 cm.
*Diameter*.—3 mm.
*Texture*.—Slightly pubescent.
*Color*.—Near Greyed-Purple N186C.
*Orientation*.—Upright.
*Strength*.—Strong and flexible.

Pedicel:

*Length*.—5 to 5 mm.
*Diameter*.—1-2 mm.
*Angle*.—About 45 degrees from attachment.
*Strength*.—Moderate.
*Texture*.—Slightly pubescent.
*Color*.—Near Greyed-Purple N186C.

REPRODUCTIVE ORGANS

Stamens:

*Number*.—About 20-30, curled and congested.
*Filament length*.—4 to 9 mm, when pulled straight.
*Filament color*.—Near Yellow-Green 150D.

Anthers:

*Shape*.—Curled.
*Length*.—1 mm.
*Color*.—Yellow 2C.
*Pollen*.—Not observed.

Pistil:

*Number*.—1.
*Length*.—2.4 cm.

Stigma:

*Shape*.—Globular.
*Color*.—Near RHS Greyed-Purple 186B.
*Ovary color*.—Near RHS Yellow 2D.

OTHER CHARACTERISTICS

Fruits and seeds: Not observed to date.

Disease/pest resistance: Observed resistance to mildew, assumed to be the pathogen *Erysiphe australiana*. Neither resistance nor susceptibility to other normal diseases and pests of *Lagerstroemia* observed.

Temperature range: Observed to tolerate a temperature range from about −2° C. to 38° C.

What is claimed is:

1. A new and distinct cultivar of *Lagerstroemia* plant named 'HOCH873' as herein illustrated and described.

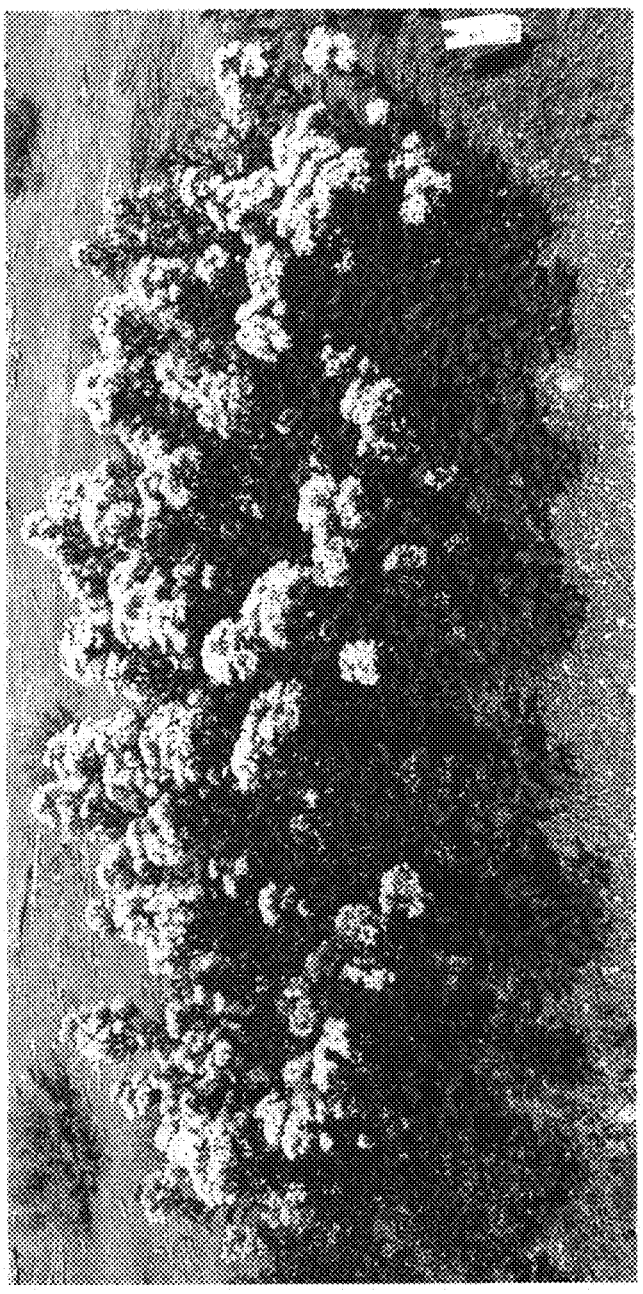

* * * * *